US012661048B2

(12) United States Patent
Keiser

(10) Patent No.: US 12,661,048 B2
(45) Date of Patent: Jun. 23, 2026

(54) SYSTEM AND METHOD FOR DETERMINING ENDURANCE OF A MUSCLE GROUP

(71) Applicant: Keiser Corporation, Fresno, CA (US)

(72) Inventor: Dennis L. Keiser, Sanger, CA (US)

(73) Assignee: Keiser Corporation, Fresno, CA (US)

( * ) Notice: Subject to any disclaimer, the term of this patent is extended or adjusted under 35 U.S.C. 154(b) by 581 days.

(21) Appl. No.: 17/938,637

(22) Filed: Oct. 6, 2022

(65) Prior Publication Data

US 2023/0115911 A1 Apr. 13, 2023

Related U.S. Application Data

(60) Provisional application No. 63/253,521, filed on Oct. 7, 2021.

(51) Int. Cl.
*A61B 5/22* (2006.01)
*A61B 5/00* (2006.01)
*A61B 5/11* (2006.01)

(52) U.S. Cl.
CPC ............ *A61B 5/224* (2013.01); *A61B 5/1121* (2013.01); *A61B 5/6895* (2013.01); *A61B 5/742* (2013.01)

(58) Field of Classification Search
CPC ..... A61B 5/224; A61B 5/1121; A61B 5/6895; A61B 5/742; A61B 2503/10; A61B 5/4519; A61B 2505/09; A63B 21/0087; A63B 23/03541; A63B 24/0062; A63B 24/0087
See application file for complete search history.

(56) References Cited

U.S. PATENT DOCUMENTS

| | | | | |
|---|---|---|---|---|
| 5,011,142 A | * | 4/1991 | Eckler .............. | A63B 21/00072 482/5 |
| 5,331,851 A | * | 7/1994 | Parviainen ............. | A61B 5/389 482/133 |
| 5,800,310 A | * | 9/1998 | Jones ................. | A63B 23/0488 482/901 |

(Continued)

FOREIGN PATENT DOCUMENTS

EP        4438138 A1 * 10/2024 ......... A63B 21/0052

OTHER PUBLICATIONS

Relationship Between Velocity Loss Andrepetitions in Reserve in the Bench Press Andback Squat Exercises, David Rodri Guez-Rosell et al., Journal of Strength and Conditioning Research, vol. 34 I No. 9 I Sep. 2020 (Year: 2020).*

(Continued)

*Primary Examiner* — Sean P Dougherty
(74) *Attorney, Agent, or Firm* — KNOBBE, MARTENS, OLSON & BEAR, LLP

(57)        ABSTRACT

An apparatus and method to evaluate the endurance of a muscle group of a user by measuring velocities of an engagement assembly coupled to a resistance element and moved by the user through a plurality of exercise strokes. A muscle group is assessed by determining a rate of fatigue for the muscle group. The method can include adjusting the controllable resistance to a resistance level, monitoring the movement of the engagement assembly against the resistance level over a plurality of repetitions, determining a relationship between the movement of the engagement assembly by the user over the plurality of repetitions, and using the relationship to determine the rate of fatigue.

23 Claims, 8 Drawing Sheets

(56) References Cited

U.S. PATENT DOCUMENTS

| | | | | |
|---|---|---|---|---|
| 7,666,118 | B1* | 2/2010 | Anthony | A63B 21/0724 |
| | | | | 482/8 |
| 9,433,815 | B1* | 9/2016 | Hughes | A63B 15/00 |
| 10,688,345 | B1* | 6/2020 | Lynch | G16H 20/30 |
| 10,814,172 | B1* | 10/2020 | Ilfrey | A63B 23/035 |
| 11,130,022 | B1* | 9/2021 | LoDuca | A63B 69/0053 |
| 11,331,536 | B1* | 5/2022 | Wood | A61B 5/1124 |
| 11,701,546 | B1* | 7/2023 | Belson | G06N 3/045 |
| | | | | 482/8 |
| 2003/0032524 | A1* | 2/2003 | Lamar | A63B 21/4029 |
| | | | | 482/8 |
| 2003/0092543 | A1* | 5/2003 | Giannelli | A63B 21/4035 |
| | | | | 482/99 |
| 2004/0250618 | A1* | 12/2004 | Keiser | A63B 21/4047 |
| | | | | 600/587 |
| 2005/0032612 | A1* | 2/2005 | Keiser | A63B 21/078 |
| | | | | 482/111 |
| 2005/0239615 | A1 | 10/2005 | Keiser | |
| 2006/0058699 | A1* | 3/2006 | Vitiello | A61B 5/389 |
| | | | | 600/546 |
| 2006/0287614 | A1* | 12/2006 | Hogan | A61B 5/224 |
| | | | | 600/595 |
| 2007/0037679 | A1* | 2/2007 | Geeting | A63B 23/0205 |
| | | | | 482/121 |
| 2007/0202992 | A1 | 8/2007 | Grasshoff | |
| 2007/0219051 | A1* | 9/2007 | Hayashino | A63B 23/0211 |
| | | | | 482/92 |
| 2007/0232453 | A1* | 10/2007 | Hanoun | A63B 21/008 |
| | | | | 482/7 |
| 2008/0058164 | A1* | 3/2008 | Douglas | A63B 21/0087 |
| | | | | 482/110 |
| 2010/0029448 | A1* | 2/2010 | Hayes | A63B 21/4047 |
| | | | | 482/112 |
| 2010/0125026 | A1* | 5/2010 | Zavadsky | A63F 9/24 |
| | | | | 482/5 |
| 2010/0197462 | A1* | 8/2010 | Piane, Jr. | A63B 21/00 |
| | | | | 482/8 |
| 2010/0216600 | A1 | 8/2010 | Noffsinger | |

| | | | | |
|---|---|---|---|---|
| 2011/0105284 | A1* | 5/2011 | Thulin | A63B 21/154 |
| | | | | 482/98 |
| 2011/0118085 | A1* | 5/2011 | Douglas | A63B 21/157 |
| | | | | 482/139 |
| 2012/0071733 | A1* | 3/2012 | Grey | G16H 20/40 |
| | | | | 600/301 |
| 2012/0184871 | A1* | 7/2012 | Jang | A61B 5/221 |
| | | | | 600/546 |
| 2012/0329615 | A1* | 12/2012 | Jeong | G16H 40/63 |
| | | | | 482/113 |
| 2013/0018102 | A1* | 1/2013 | Dente, III | A23L 33/10 |
| | | | | 514/574 |
| 2014/0137647 | A1* | 5/2014 | Kim | A61B 5/389 |
| | | | | 73/379.01 |
| 2015/0141200 | A1* | 5/2015 | Murray | A63B 22/0087 |
| | | | | 482/52 |
| 2016/0023043 | A1* | 1/2016 | Grundy | A63B 59/00 |
| | | | | 482/8 |
| 2017/0100628 | A1* | 4/2017 | Wilt | A63B 24/0087 |
| 2018/0140901 | A1* | 5/2018 | Wiebe | A63B 24/0006 |
| 2019/0054339 | A1* | 2/2019 | Price | A63B 21/4043 |
| 2019/0192913 | A1* | 6/2019 | Hwang | G09B 19/0038 |
| 2021/0008413 | A1* | 1/2021 | Asikainen | G06F 3/0304 |
| 2021/0339067 | A1* | 11/2021 | Sims, Jr. | A63B 21/4049 |
| 2022/0296966 | A1* | 9/2022 | Asikainen | G16H 20/30 |
| 2023/0337967 | A1* | 10/2023 | Johns | A61B 5/4571 |
| 2024/0149101 | A1* | 5/2024 | Klassen | A63B 21/169 |

OTHER PUBLICATIONS

Williams, J. H., et al. "A constant-load ergometer for measuring peak power output and fatigue." *Journal of applied physiology* 65.5 (1988): 2343-2348.
International Search Report issued in PCT/US2022/077698, dated Jan. 24, 2023.
Rodriguez-Rosell David et al: "Relationship Between Velocity Loss and Repetitions in Reserve in the Bench Press and Back Squat Exercises", Journal of Strength and Conditioning Research, vol. 34, No. 9, Sep. 1, 2020 (Sep. 1, 2020), pp. 2537-2547, XP093354078, us ISSN: 1064-8011, DOI: 10.1519/JSC.0000000000002881.

* cited by examiner

SYSTEM AND METHOD FOR DETERMINING ENDURANCE OF A MUSCLE GROUP

CROSS-REFERENCE TO RELATED APPLICATIONS

This application claims the benefit of U.S. Provisional Application No. 63/253,521, filed Oct. 7, 2021, the entire disclosure of which is hereby incorporated by reference in its entirety.

BACKGROUND

Field

The present invention is applicable to the fields of fitness, exercise, physical rehabilitation, sports medicine and extremity testing and is directed to methods and apparatuses useable in such fields.

Description of the Related Art

Numerous devices have been developed to increase the strength, agility and quickness of athletes and other persons. In addition to enhancing the performance of athletes, such devices are used to improve or maintain the fitness and health of non-athletes, both to enhance the lifestyles of non-athletes and to potentially increase their respective life spans. Such devices range from basic equipment such as barbells, dumbbells, and the like, to increasingly more complex equipment such as universal gyms which enable a user to quickly modify the weights or resistances being used to exercise the user's muscles. See, for example, U.S. Pat. Nos. 4,257,593; 5,526,692; 5,336,145; 6,962,554; 7,172,538; 7,686,749; 7,998,038; 8,052,584; 8,3231,58; and U.S. Pat. No. 8,523,789 to Dennis L. Keiser, which describe exercising apparatuses and related devices that employ pneumatic devices to provide controllable resistances, and which are each incorporated by reference in their entirety. In particular, such pneumatic exercising apparatuses advantageously reduce or eliminate the inertial effects of conventional weights wherein the force required to start moving a weight and the tendency of the weights to continue moving cause the forces required during each exercising stroke to vary throughout the stroke. Such pneumatic apparatuses provide a generally constant resistance throughout the exercising stroke.

In addition to being used for the development of strength, agility and quickness, exercising apparatuses can be used to measure strength, agility and quickness of a person. For example, a person's ability to lift weights against the force of gravity or a corresponding ability to move against a resistance can be measured at different times to determine whether such characteristics are improving in response to an exercise program or in response to therapy. Such measurements can also be used for evaluation purposes to determine whether one or more muscles or muscle groups are not performing adequately so that a therapist or a fitness trainer, for example, can develop a program of therapy or training more specifically directed to the inadequately performing muscles.

Historically, measurement and evaluation of muscular performance have concentrated on measuring the strength of a muscle or muscle group (e.g., measuring the amount of weight that can be lifted). However, it has been determined that strength alone does not accurately represent the performance of muscles. A person's muscles may be able to lift an adequate amount of weight, but may fatigue over time. For example, a 5% drop in a 100-meter sprinter's power output of any of the muscles involved in sprinting can make the difference between setting a new world record or not even making the podium. Likewise, an older adult's inability to maintain a certain level of power output over time can increase the likelihood of instability, falling, and even breaking a hip or worse. Knowing this information beforehand and being able to train the deficiencies will raise human performance at all levels and reduce the potential of injury.

SUMMARY

The systems and methods of the present invention have several features, no single one of which is solely responsible for its desirable attributes. Without limiting the scope, as expressed by the claims that follow, the more prominent features will be briefly discussed here. After considering this discussion, and particularly after reading the section entitled "Detailed Description of Certain Embodiments," one will understand how the features of this invention provide several advantages in improving human performance.

In view of the foregoing, it can be seen that a need exists for an improved apparatus and method for enabling an athlete or other user to determine their rate of physical fatigue for a given muscle group. Physical exertion is followed by physical fatigue. Measuring the level of physical exertion and the rate of physical fatigue can be important in the assessment of an individual's ability to perform at a certain level and for how long.

An aspect includes a method for assessing a rate of fatigue for a muscle group on an exercise apparatus having an engagement assembly movable against a controllable resistance by the muscle group of a user and having a monitoring system that measures a velocity of movement of the engagement assembly. The method comprises adjusting the controllable resistance to a resistance level, monitoring the movement of the engagement assembly against the resistance level over a plurality of repetitions, determining a peak speed and/or an average speed for each repetition of the plurality of repetitions, using the resistance level, the peak speed, and/or the average speed to determine a relationship between the movement of the engagement assembly by the user over the plurality of repetitions, and using the relationship to determine the rate of fatigue.

A further aspect includes wherein the movement of the engagement assembly relates to power.

A further aspect includes wherein the movement of the engagement assembly relates to velocity.

A further aspect includes wherein the resistance level is selected based on percentage body weight.

A further aspect includes determining a peak power and/or an average power for each repetition of the plurality of repetitions.

A further aspect includes displaying the peak power and/or the average power for each repetition of the plurality of repetitions.

A further aspect includes determining a total of the peak power and/or a total of the average power over the plurality repetitions.

A further aspect includes displaying the total of the peak power and/or the total of the average power over the plurality repetitions.

A further aspect includes the plurality of repetitions being performed at a maximum velocity.

A further aspect includes a concentric phase of each repetition of the plurality of repetitions is performed at a maximum velocity.

A further aspect includes wherein each repetition of the plurality of repetitions is a fixed time.

A further aspect includes the fixed time is 1 second.

A further aspect includes the concentric phase of each repetition of the plurality of repetitions is timed for a given velocity through a Range of Motion (ROM).

A further aspect includes an end point corresponds to a final repetition of the plurality of repetitions.

A further aspect includes the end point is based on time.

A further aspect includes the end point is based on number of repetitions.

A further aspect includes the end point is based on a total of the peak power and/or a total of the average power.

A further aspect includes assessing a rate of fatigue for a second muscle group, and comparing the rate of fatigue for the muscle group to the rate of fatigue for the second muscle group.

An aspect includes a method for assessing a rate of fatigue for a muscle group on an exercise apparatus having an engagement assembly movable against a controllable resistance by the muscle group of a user and having a monitoring system that measures a velocity of movement of the engagement assembly. The method comprises adjusting the controllable resistance to a resistance level, monitoring the movement of the engagement assembly against the resistance level over a plurality of repetitions, determining a relationship between the movement of the engagement assembly by the user over the plurality of repetitions, and using the relationship to determine the rate of fatigue.

A further aspect includes wherein the movement of the engagement assembly relates to power.

A further aspect includes wherein the movement of the engagement assembly relates to velocity.

An aspect includes an apparatus for assessing a rate of fatigue for a muscle group. The apparatus comprises a controllable resistance, an engagement assembly movable against the controllable resistance by using the muscle group of a user, a monitoring system configured to measure a velocity of movement of the engagement assembly over a plurality of repetitions to determine a relationship between the movement of the engagement assembly by user over the plurality of repetitions, and determine the rate of fatigue using the relationship.

A further aspect comprises a display unit that displays the rate of fatigue.

A further aspect includes wherein the controllable resistance is a pneumatic device.

A further aspect includes wherein the engagement assembly comprises a left lever and a right lever.

A further aspect includes wherein the movement of the engagement assembly relates to power.

A further aspect includes wherein the movement of the engagement assembly relates to velocity.

BRIEF DESCRIPTION OF THE DRAWINGS

These and other features, aspects, and advantages of the present invention will now be described in connection with the disclosure, in reference to the accompanying drawings. The illustrated embodiments, however, are merely examples and are not intended to limit the disclosure.

4

Figure 1:
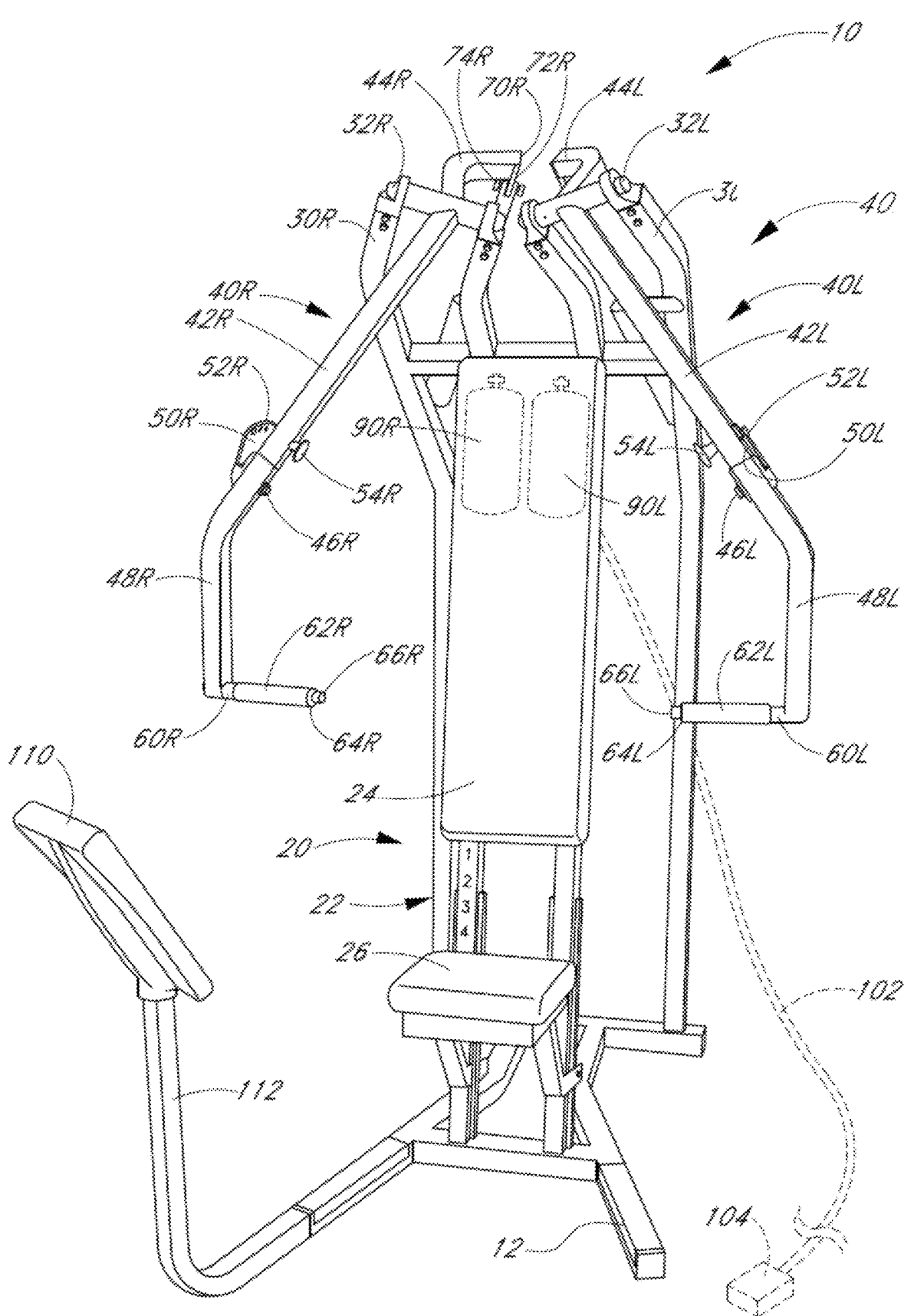
FIG. 1 illustrates a perspective view of an embodiment of an exemplary exercise apparatus that can assess a rate of fatigue for a muscle group.
Figure 2:
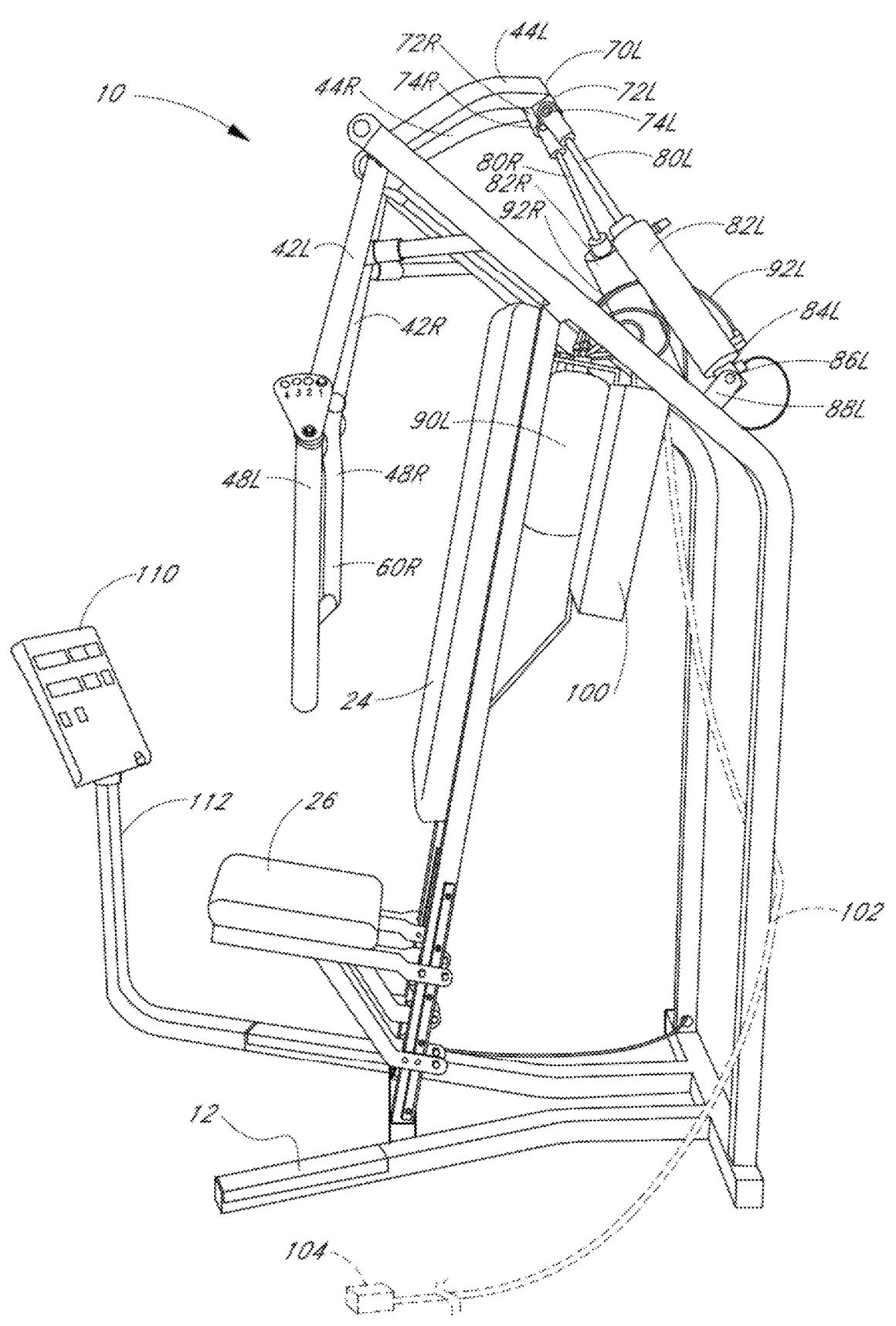

FIG. 2 illustrates a side view of the exemplary exercise apparatus from FIG. 1.

Figure 3:
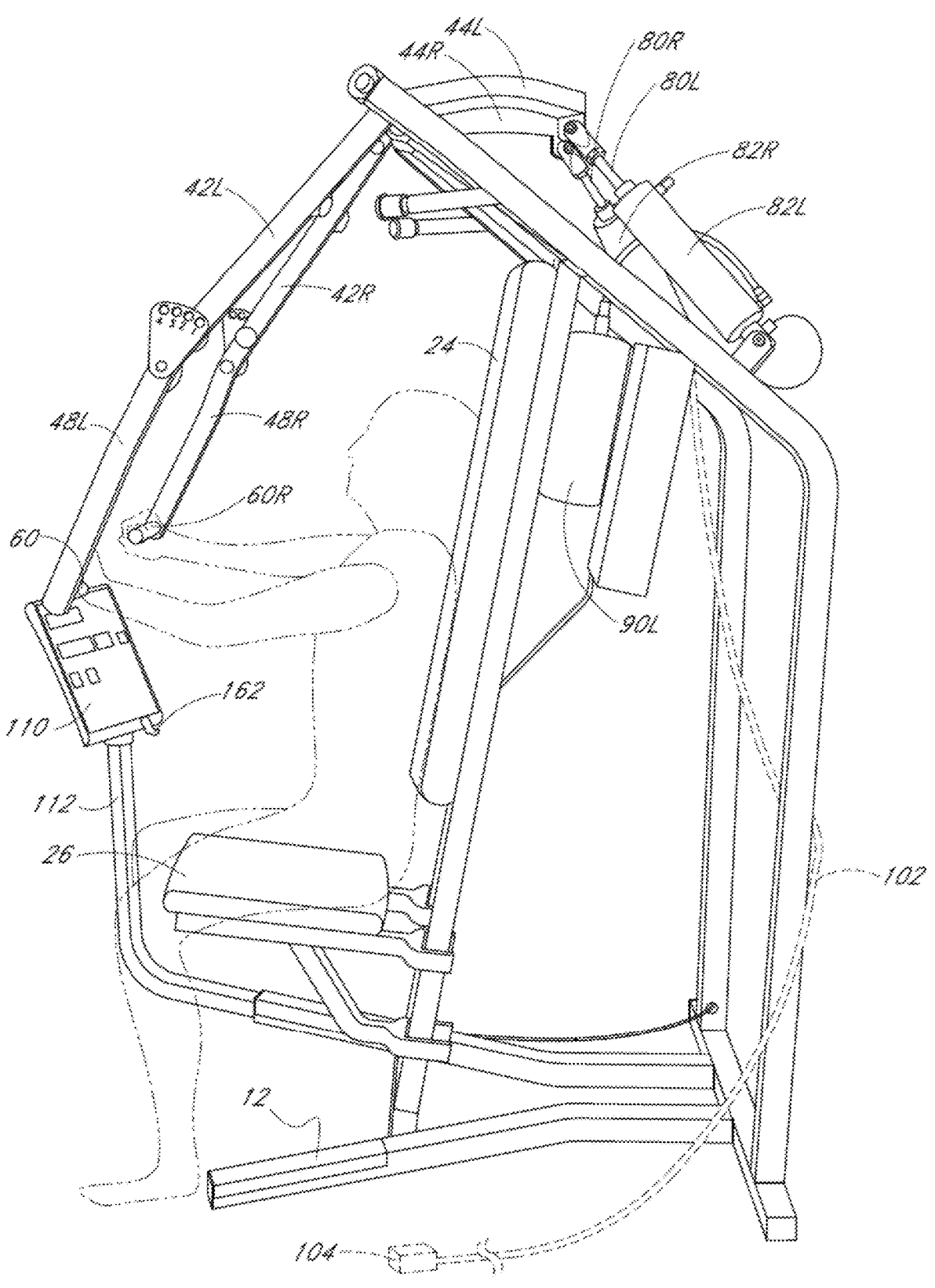

FIG. 3 is similar to FIG. 2 except the exemplary exercise apparatus is in use.

Figure 4:
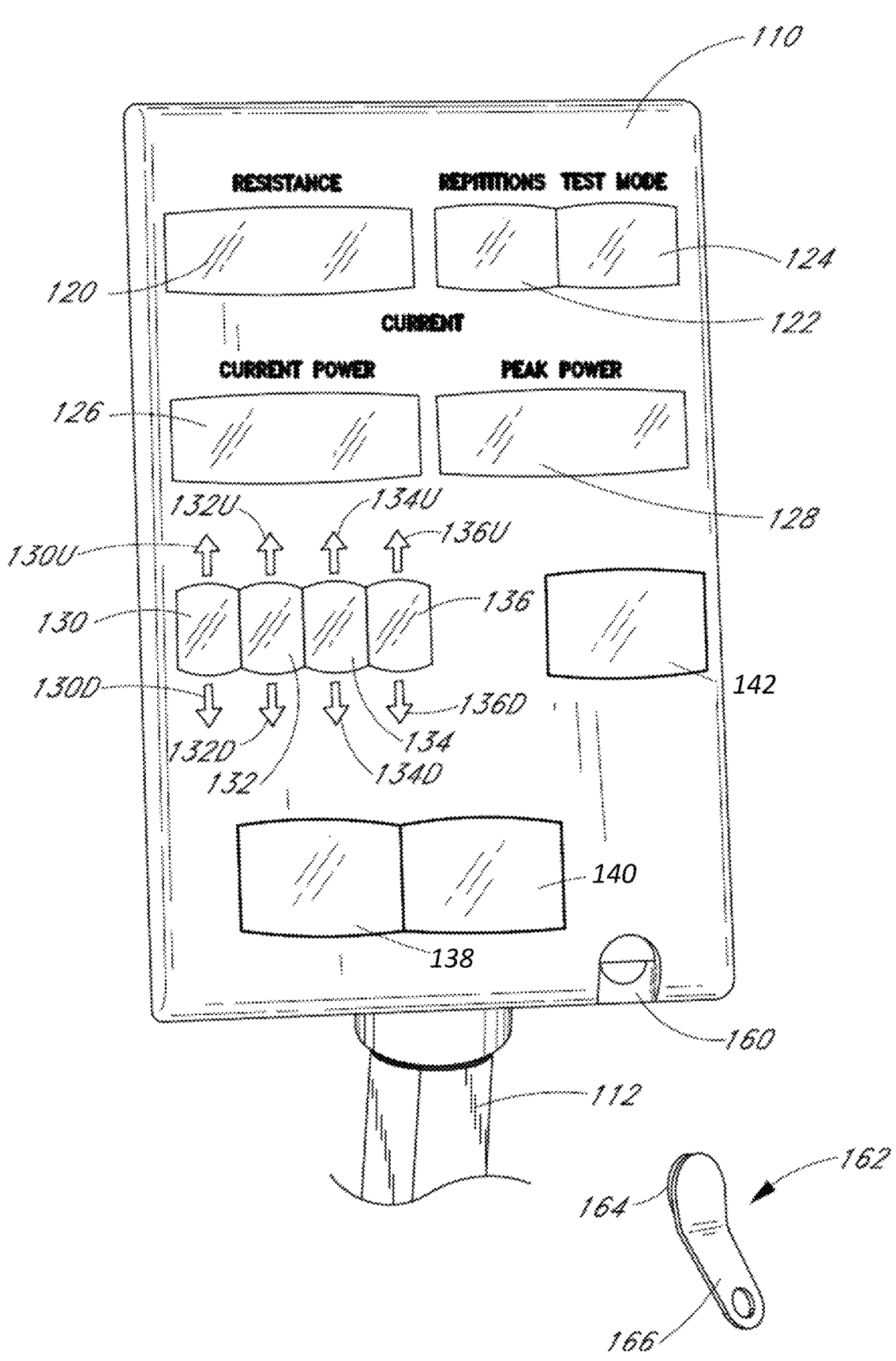

FIG. 4 illustrates an exemplary embodiment of a display unit of the exemplary exercise apparatus of FIG. 1.

Figure 5:
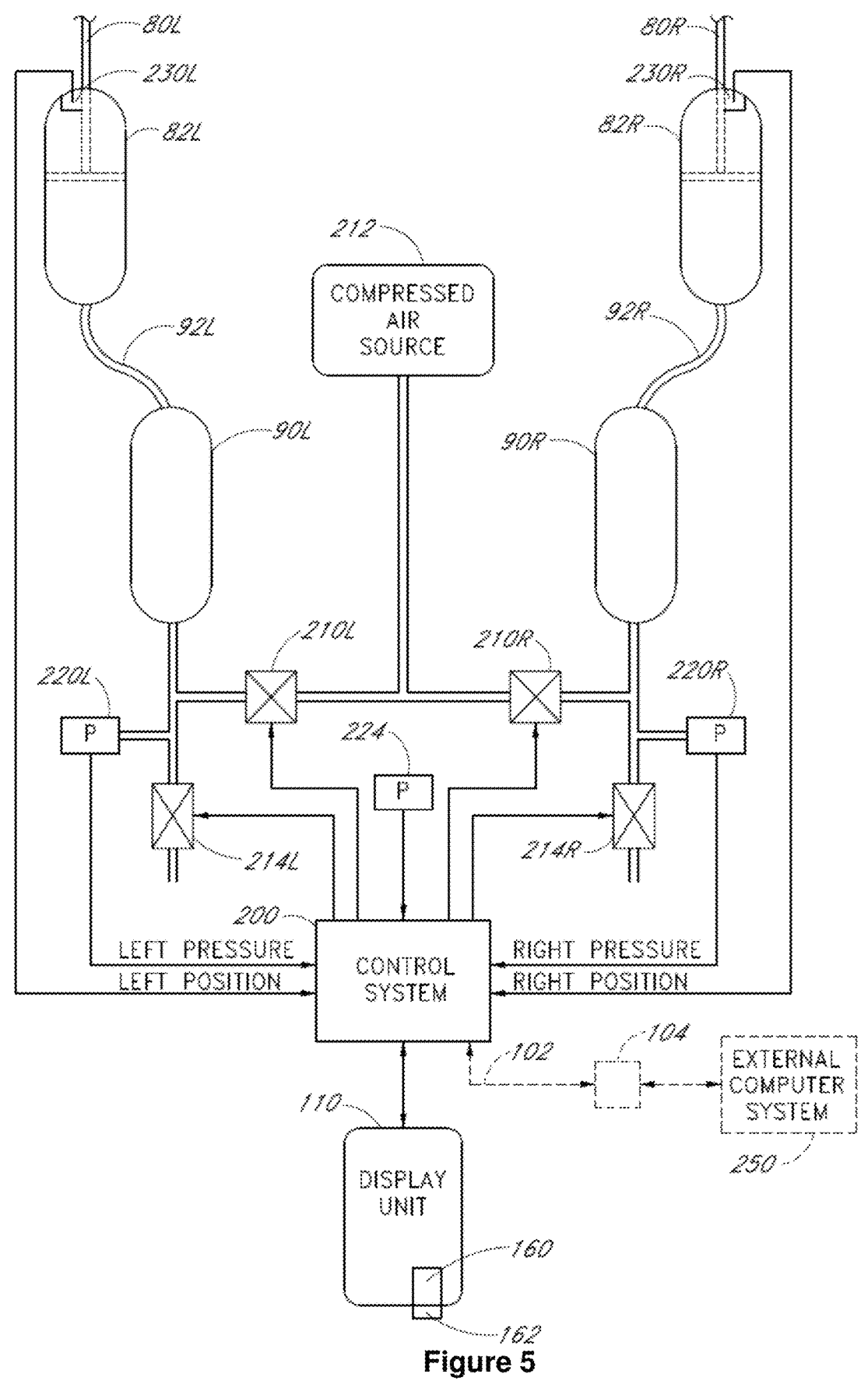

FIG. 5 illustrates a block diagram of an embodiment of a pneumatic system and a control system for the exemplary exercise apparatus of FIG. 1 that includes a first configuration of control valves.

Figure 6:
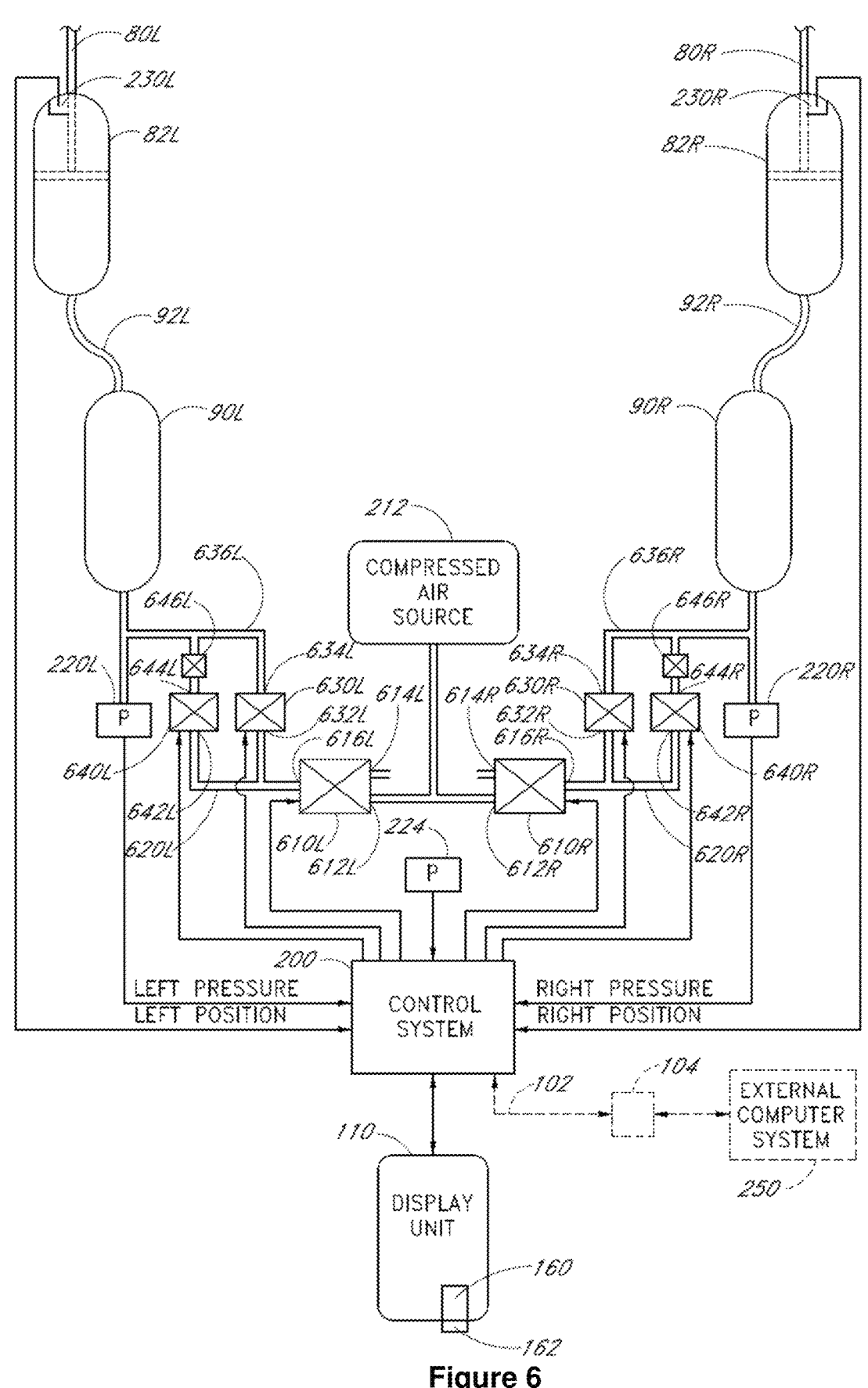

FIG. 6 illustrates a block diagram of another embodiment of a pneumatic system and a control system for the exemplary exercise apparatus of FIG. 1 that includes a second configuration of control valves.

Figure 7:
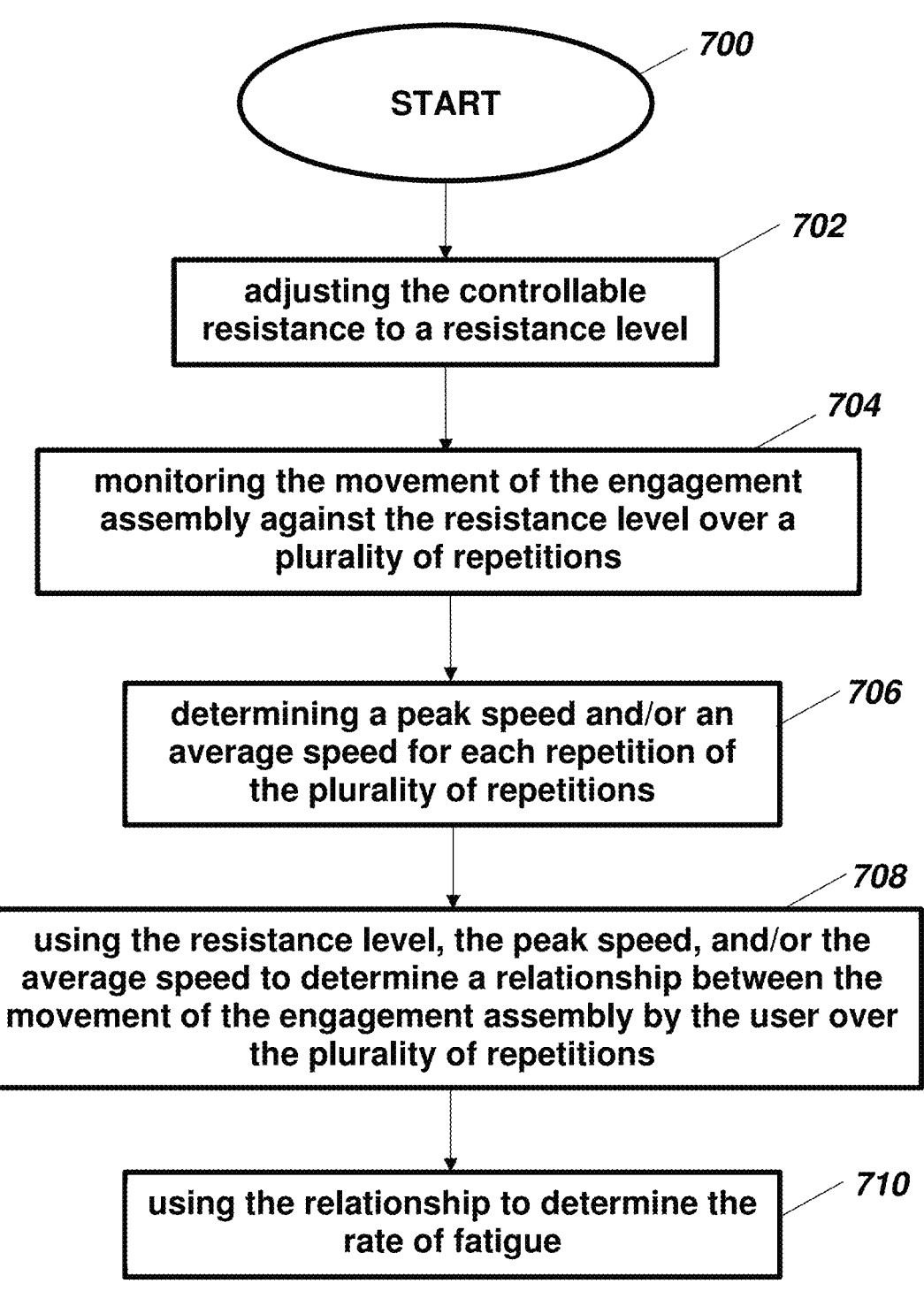

FIG. 7 illustrates a flow chart of an exemplary method for performing an endurance or fatigue test that employs a relationship between movement of an engagement assembly by the user over a plurality of repetitions to determine a rate of fatigue in accordance with the disclosure.

Figure 8:
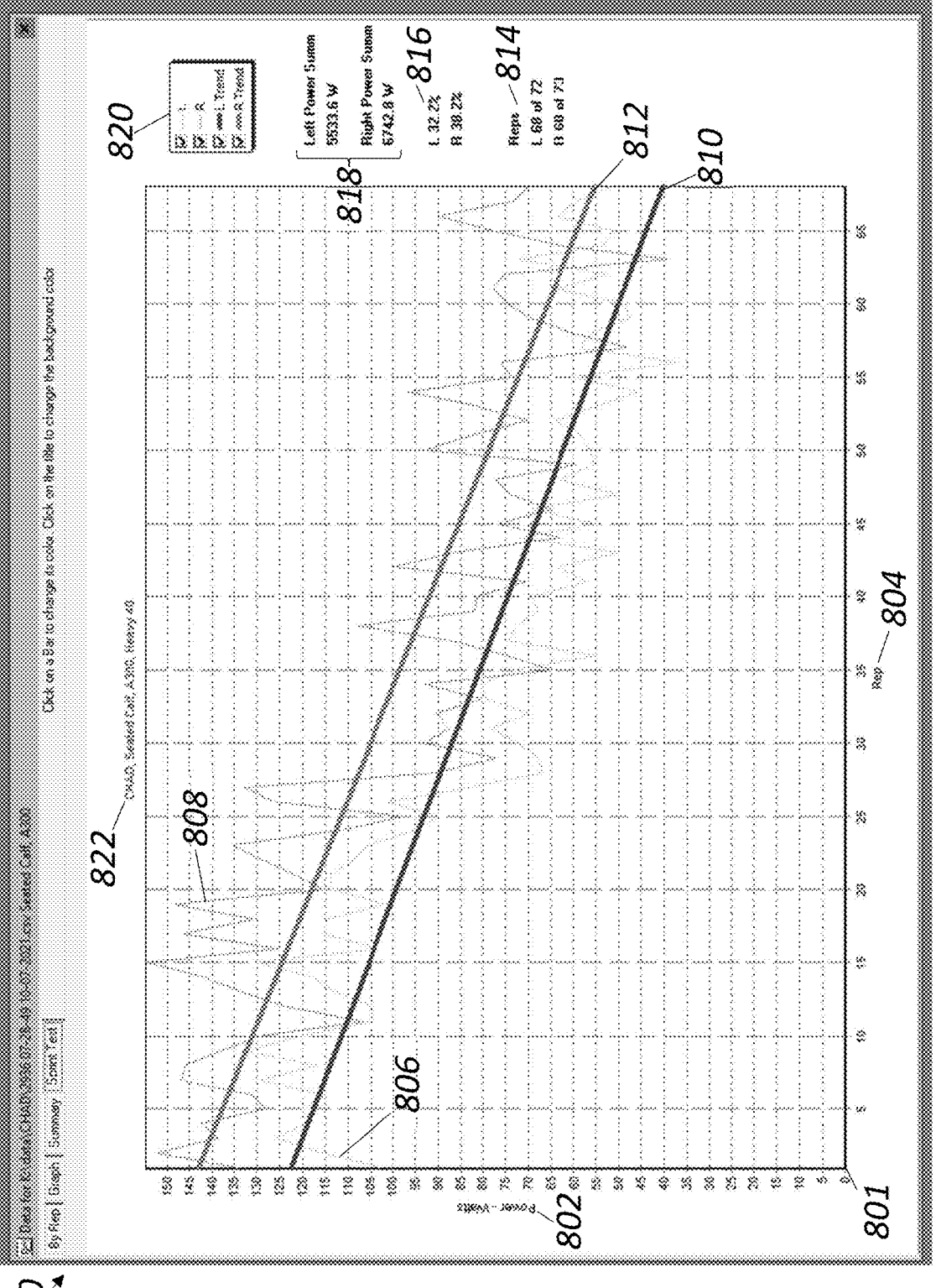

FIG. 8 illustrates a graphical data output of the endurance or fatigue test performed in accordance with the method of FIG. 7.

DETAILED DESCRIPTION OF CERTAIN EMBODIMENTS

U.S. Pat. Nos. 4,257,593; 5,526,692; 5,336,145; 6,962,554; 7,172,538; 7,686,749; 7,998,038; 8,052,584; 8,3231,58; and U.S. Pat. No. 8,523,789 to Dennis L. Keiser, incorporated by reference in their entireties, disclose embodiments of exemplary exercise apparatuses that can be used advantageously in connection with embodiments of the present invention for evaluating endurance. Although referenced herein to the apparatuses disclosed in U.S. Pat. Nos. 4,257,593; 5,526,692; 5,336,145; 6,962,554; 7,172,538; 7,686,749; 7,998,038; 8,052,584; 8,3231,58; and 8,523,789, it should be understood that embodiments of the present invention can be incorporated into other exercise apparatuses. Examples of exercise equipment on which the endurance measurement system can be used include, without limitation, a leg press, a leg extension machine, a leg curl machine, a standing hip machine, an abdominal machine, a lower back machine, an upper back machine, a lateral pull down machine, a military press machine, a triceps machine, an arm curl machine, a seated butterfly machine, a seated calf machine, a lateral shoulder raise machine, a squat machine, and a hip abductor machine, such as, for example, the types available commercially from Keiser Corporation, Fresno, California.

As briefly discussed above, one particularly advantageous use for the embodiment described herein is to perform a power/speed fatigue test to determine a user's level of physical exertion and their rate of physical fatigue for the muscle groups that are exercised by a particular machine (e.g., machines disclosed in U.S. Pat. Nos. 4,257,593; 5,526,692; 5,336,145; 6,962,554; 7,172,538; 7,686,749; 7,998,038; 8,052,584; 8,3231,58; and 8,523,789). With this information, a user is able to exercise the muscle groups to improve their rate of fatigue and to strive to raise their performance levels and reduce the potential of injury.

In certain embodiments, the method assesses a rate of fatigue of a muscle group. In certain embodiments, the method assesses the rate of fatigue for the muscle group on an exercise apparatus. In certain embodiments, the exercise apparatus has an engagement assembly movable against a controllable resistance by the muscle group of a user. In certain embodiments, the exercise assembly has a monitoring system that measures a velocity of movement of the engagement assembly.

FIG. 1 illustrates a perspective view of an embodiment of an exemplary exercise apparatus 10 that can assess a rate of fatigue for a muscle group. The illustrated exercise apparatus 10 is configured as a "chest press", however, the disclosure is not so limited. Although described herein with respect to a chest press, it should be understood that embodiments of the present disclosure can be incorporated into other exercise apparatuses that test the same or other muscle groups. FIG. 2 illustrates a side view of the exercise apparatus 10 from FIG. 1. The exercise apparatus 10 can be used advantageously in connection with embodiments of the present disclosure for evaluating the rate of fatigue of particular muscle groups.

In certain embodiments, the apparatus 10 comprises a frame 12 having a lower portion that rests on a floor of an exercise facility or a fitness evaluation facility. In certain embodiments, the frame 12 has a generally vertical front portion 20 that supports a seat assembly 22. In certain embodiments, the seat assembly 22 comprises a seat back portion 24 and a seat bottom portion 26. In certain embodiments, the seat bottom portion 24 is adjustable vertically to accommodate variations in the physical characteristics of users. In certain embodiments, the seat back portion 24 is also adjustable to accommodate variations in lengths of the users' arms.

In certain embodiments, the frame 12 includes a left top portion 30L and a right top portion 30R. In certain embodiments, the two top portions 30L, 30R are cantilevered over the seat assembly 22. In certain embodiments, the left top portion 30L has a left hinge 32L positioned at the most forward and upward end. Similarly, the right top portion 30R has a right hinge 32R positioned at the most forward and upward end. As used herein, "left" and "right" are defined with respect to the position of a user of the apparatus 10. Thus, in the view shown in FIG. 1, the left top portion 30L and the left hinge 32L are on the right side of the drawing figure, and the right top portion 30R and the right hinge 32R are on the left side of the drawing figure.

In certain embodiments, an engagement assembly 40 is movable against a controllable resistance by a muscle group of a user. In certain embodiments, the apparatus 10 further comprises a monitoring or control system 200 that measures a velocity of movement of the engagement assembly 40. In the illustrated embodiment, the engagement assembly 40 comprises a left lever 40L and a right lever 40R. In certain embodiments, the left lever 40L is pivotally mounted to the left hinge 32L, and the right lever 40R is pivotally mounted to the right hinge 32R. As described below, the left lever 40L and the right lever 40R in combination with their respective components each comprises an independent engagement apparatus for coupling the power from a user to respective resistance elements. In certain embodiments, the controllable resistance is in the form of resistance elements implemented by left and right pneumatic cylinders, which are also described below.

In certain embodiments, the left lever 40L comprises a lower lever portion 42L that extends generally below and slightly forward of the left hinge 32L. In certain embodiments, the left lever 40L further comprises an upper lever portion 44L that extends generally above and to the rear of the left hinge 32L. In the illustrated embodiment, the lower lever portion 42L and the upper lever portion 44L comprise a unitary structure having the left hinge 32L formed at an intermediary location of the structure such that when the lower lever portion 42L moves forward and generally upward, the upper lever portion 44L moves rearward and generally downward.

Preferably, the lower lever portion 42L includes a hinge 46L at the lower end thereof. An extended lever portion 48L pivotally mounted to the lower lever portion 42L via the hinge 46L. An adjustment selector 50L is mounted to the extended lever portion 48L at the location of the hinge 46L. In certain embodiments, the adjustment selector 50L has a plurality of holes 52L formed therein (e.g., four holes in the illustrated embodiment). In certain embodiments, the holes 52L are selectably engageable with a spring-loaded pin 54L near the lower end of the lower lever portion 42L. In certain embodiments, the spring-loaded pin 54L can be temporarily disengaged from one of the holes 52L and the extended lever portion 48L can be pivoted about the hinge 46L to change the angle of the extended lever portion 48L with respect to the lower lever portion 42L to adapt the position of the extended lever portion 48L to the physical characteristics of a particular user. In certain embodiments, the spring-loaded pin 54L is re-engaged the most closely aligned one of the holes 52L to restrain the extended lever portion 48L at the selected angle.

In like manner, the right lever 40R comprises elements that generally correspond to the elements of the left lever 40L. In certain embodiments, the elements of the right lever 40R are positioned in similar locations and operate in similar manners as the corresponding elements of the left lever 40L. In particular, the right lever 40R comprises a lower lever portion 42R, an upper lever portion 44R, a hinge 46R, and an extended lever portion 48R. An adjustment selector 50R has a plurality of holes 52R. A selectable one of the holes 52R is engageable with a spring-loaded pin 54R to adjust the angle of the extended lever portion 48R with respect to the lower lever portion 42R.

In alternative embodiments, the extended lever portions 48L, 48R may be positioned at a fixed angle with respect to the respective lower lever portions 42L, 42L such that the hinges 46L, 46R and the selectors 50L, 50R are not needed.

In certain embodiments, the left lever 40L includes a left handgrip 60L that extends inward (e.g., towards the right) from the left extended lever portion 48L. Similarly, the right lever 40R includes a right handgrip 60R that extends inward (e.g., towards the left) from the right extended lever portion 166. In the illustrated embodiment, the handgrips 60L, 60R are positioned generally perpendicularly to the respective extended lever portions 48L, 48R. Each handgrip 60L, 60R has a length sufficient to accommodate the width of a user's hand and to further accommodate variations in the position of a user's hand. Preferably, each handgrip 60L, 60R is cylindrical and has a respective gripping surface 62L, 62R mounted thereon to assist a user in grasping the handgrips. In certain embodiments, the gripping surfaces 62L, 62R may advantageously be padded for the comfort of the user's hands.

In certain embodiments, the exposed end 64L of the left handgrip 60L supports a left actuator button 66L. Similarly, the exposed end 64R of the right handgrip 60R supports a right actuator button 66R. By pressing one of the actuator buttons 66L or 66R or by pressing both buttons 66L and 66R, a user is able to control various aspects of the operation of the apparatus 10, which will be discussed below.

FIG. 3 is similar to FIG. 2 except the exemplary exercise apparatus is in use by a user. In certain embodiments, the user is seated in the seat assembly 22 and is able to grip the handgrips 60L, 60R and apply forward forces to the extended lower portions 48L, 48R of the levers 40L, 40R to cause the extended lower portions 48L, 48R to move generally forwardly and upwardly. In certain embodiments, the levers 40L, 40R pivot about the respective hinges 32L, 32R such that the respective upper lever portions 44L, 44R move generally rearward and downward.

Note that in the illustrated embodiment, the left lever 40L and the right lever 40R operate substantially independently. For example, one lever can be moved while the other lever remains at rest. As a further example, the two levers can be moved at different rates. In alternative embodiments (not shown), the two levers can be advantageously interconnected to move as a unit when the ability to exercise each arm independently is not needed.

A rearmost end 70L of the left upper lever portion 44L includes a left upper pivot mount 72L. In certain embodiments, the left upper pivot mount 72L supports a pivot pin 74L. A left connecting rod 80L extends from a first end of a left pneumatic cylinder 82L and is connected to the left upper lever portion 44L at the left upper pivot mount 72L via the pivot pin 74L.

A second end of the left pneumatic cylinder 82L includes a lug 84L having a pivot pin 86L mounted therein. In certain embodiments, the pivot pin 86L engages a left lower pivot mount 88L on a generally rearward portion of the left top portion 30L of the frame 12. Movement of the left upper lever portion 44L rearwardly and downwardly in response to forward force applied to the left handgrip 60L by a user causes the left connecting rod 80L to be moved into the left pneumatic cylinder 82L. An end (not shown) of the left connecting rod 80L comprises a piston that slides within the left pneumatic cylinder 82L. In certain embodiments, the left connecting rod 80L and the left pneumatic cylinder 82L comprise a linear actuator which functions as a resistance assembly for the left lever 40L. As the left connecting rod 80L moves into the left pneumatic cylinder 82L, the left connecting rod 80L pivots with respect to the left upper pivot mount 72L, and the second end of the left pneumatic cylinder 82L pivots with respect to the left lower pivot mount 88L so that the left connecting rod 80L can move freely with respect to the left pneumatic cylinder 82L without binding.

Similarly, an end 70R of the right upper lever portion 44R includes a right upper pivot mount 72R. In certain embodiments, the right upper pivot mount 72R supports a pivot pin 74R. A right connecting rod 80R extends from a first end of a right pneumatic cylinder 82R and is connected to the right upper lever portion 44R at the right upper pivot mount 72R via the pivot pin 72R.

A second end (not shown) of the right pneumatic cylinder 82R includes a lug (not shown) having a pivot pin (not shown) mounted therein. In certain embodiments, the pivot pin engages a right lower pivot mount (not shown) on a generally rearward portion of the right top portion 30R of the frame 12. Movement of the right upper lever portion 44R rearwardly and downwardly in response to forward force applied to the right handgrip 60R by a user causes the right connecting rod 80R to be moved into the right pneumatic cylinder 82R. An end (not shown) of the right connecting rod 80R comprises a piston that slides within the right pneumatic cylinder 82R. In certain embodiments, the right connecting rod 80R and the right pneumatic cylinder 82R comprise a linear actuator which functions as a resistance assembly for the right lever 40R. As the right connecting rod 80R moves into the right pneumatic cylinder 82R, the right connecting rod 80R pivots with respect to the right upper pivot mount 72R, and the second end of the right pneumatic cylinder 82R pivots with respect to the right lower pivot mount so that the right connecting rod 80R can move freely with respect to the right pneumatic cylinder 82R without binding.

Within each pneumatic cylinder 82L, 82R, the respective piston divides the cylinder body into two variable volume chambers. At least one of the chambers is a charged chamber that selectively communicates with a compressed air source (shown schematically in FIGS. 5 and 6) and with the atmosphere so as to provide the desired resistance. In certain embodiments, the other chamber can be open to the atmosphere; however, in some applications, both chambers can be pressurized (e.g., be of equal pressure), can selectively communicate with the atmosphere and/or can communicate with each other. In the illustrated embodiment, however, one of the chambers communicates with the atmosphere so as not to resist movement of the piston.

In certain embodiments, the pneumatic cylinders 82L, 82R may be constructed from metal or other suitable materials. In certain embodiments, the pneumatic cylinders 82L, 82R and the internal pistons comprise a polymer (e.g., plastic) to reduce the manufacturing costs and the weight of the resistance assemblies.

In the illustrated embodiment, the respective connecting rod 80L, 80R extends through the variable volume chamber open to the atmosphere. In certain embodiments, the respective connecting rod 80L, 80R moves linearly along a stroke axis as the piston slides within the cylinder bore in the respective pneumatic cylinder 82L, 82R. In certain embodiments, the stroke lengths of the connecting rods 80L, 80R are sufficient to provide the desired strokes for the upper lever portions 44L, 44R.

In the illustrated embodiment, the internal chamber proximate the respective second end of each pneumatic cylinder 82L, 82R (e.g., the lower chamber of each cylinder) is pressurized. In certain embodiments, the lower chamber of the left pneumatic cylinder 82L communicates with at least one left accumulator 90L via a pneumatic tube 92L, as shown more clearly in FIG. 5. Similarly, the lower chamber of the right pneumatic cylinder 82R communicates with at least one right accumulator 90R via a pneumatic tube 92R. In certain embodiments, the two accumulators 90L, 90R are located behind the seat back portion 24 in the illustrated embodiment and are secured to the frame 12. In certain embodiments, the pneumatic tubes 92L, 92R function as respective air equalization lines that interconnect the accumulators 90L, 90R with the respective pneumatic cylinders 82L, 82R so as to expand effectively the variable volumes of the lower chambers of the two cylinders. In this manner, the effective air volume of the cylinder is increased, and air pressure thus will not increase as dramatically when the piston is moved.

Each accumulator 90L, 90R and the respective upper chamber within the pneumatic cylinders 82L, 82R also selectively communicate with the compressed air source (FIG. 5) and with the atmosphere. In the illustrated example, the compressed air source may be, for example, an air compressor, which can be remotely disposed relative to the exercise apparatus. In certain embodiments, the compressed air source communicates with the upper chambers through a respective inlet valve (shown schematically in FIG. 5). In the illustrated embodiment, the inlet valves for both pneumatic cylinders 82L, 82R are controlled by the left actuator button 66L on the left handgrip 60L when a user manually controls the resistance of the two pneumatic cylinders. In certain embodiments, the left actuator button 66L is selectably activated by a user to actuate the inlet valves to add air pressure to the lower chamber of each pneumatic cylinder 82L, 82R. In certain embodiments, the lower chamber is also referred to as the charged side of each cylinder.

In certain embodiments, the apparatus 10 further includes a control unit enclosure 100 that houses a monitoring or control system 200 (described in more detail below in connection with FIGS. 5-6). In certain embodiments, the monitoring or control system 200 within the enclosure 100 is optionally capable of communicating with an external computer system 250 (FIGS. 5 and 6) via a communications cable 102, an adapter unit 104 (both shown in phantom to indicate that the elements are optional), and/or wirelessly. In certain embodiments, the communications cable 102, the adapter unit 104 and the external computer system 250 are not necessary to an understanding of embodiments described herein and will not be discussed further.

FIG. 4 illustrates an exemplary embodiment of a display unit 110 of the exemplary exercise apparatus 10 of FIG. 1. In certain embodiments, the display unit 110 is supported on a riser 112 so that the display unit 110 is positioned in front of the user seated in the seat assembly 22.

As shown in FIG. 4, the display panel may include a RESISTANCE indicator 120 that displays the total resistance applied to the two handgrips 60L, 60R. In the embodiment described herein, the total resistance may be selected by a user by selectively activating the right actuator button 66R to increase the resistance and selectively activating the left actuator button 66L to decrease the resistance. In alternative embodiments, the resistance may also be selected automatically. In certain embodiments, the resistance is displayed as the force (in pounds or kilograms) required to move the handgrips 60L, 60R and is calibrated to be equivalent to the force required to move a corresponding stack of conventional weights.

In alternative embodiments of the apparatus 10 in which handgrips are not used or where hand-operated actuators cannot be readily incorporated, the controls for increasing and decreasing the resistance may be implemented as foot pedals (not shown).

In certain embodiments in which the display unit 110 and monitoring or control system 200 are powered by batteries rather than by AC power, the resistance indicator 120 is advantageously caused to display OFF rather than a resistance value in order to indicate that the monitoring or control system 200 and display unit 110 have gone into a low power consumption (e.g., "sleep") mode to increase battery life. A user wanting to activate a system in the low power consumption mode can push one of the resistance change buttons (e.g., the left actuator button 66L or the right actuator button 66R in the illustrated embodiment, or a foot pedal in an alternative embodiment) or the user can insert a data key 162. In certain embodiments, the resistance indicator can also be advantageously used to display the characters Loba to indicate that the batteries supplying the monitoring or control system 200 and the display unit 110 are low and need to be replaced.

In certain embodiments, the display unit 110 may include one or more of a REPETITIONS indicator 122, a TEST MODE indicator 124, a CURRENT POWER indicator 126, and a PEAK POWER indicator 128. In certain embodiments, the display unit 110 may include one or more of a PEAK SPEED indicator 138, an AVERAGE SPEED indicator 140, and a RATE OF FATIGUE indicator 142.

In certain embodiments, the display unit 110 may include one or more of a first machine adjustment indicator 130, a second machine adjustment indicator 132, a third machine adjustment indicator 134, and a fourth machine adjustment indicator 136. In certain embodiments, the display unit 110 may include respective up arrows 130U, 132U, 134U, 136U, above the respective machine adjustment indicators, and includes respective down arrows 130D, 132D, 134D, 136D, below the respective machine adjustment indicators. Each of the up arrows and down arrows defines a respective location of a switch beneath the faceplate of the display unit 110. Each switch can be selectively activated by a user pressing on the respective arrow.

In certain embodiments, the machine adjustment indicators 130, 132, 134, 136 are used to indicate various settings of the apparatus 10 that can be adjusted by users to accommodate differences in body structures. For example, in the embodiment described herein, the first adjustment indicator 130, for example, is assigned to indicate the vertical position of the seat bottom portion 24 of the seat assembly 22. In the illustrated embodiment, the second adjustment indicator 132, for example, is assigned to indicate the position of arm adjustment selectors 50L, 50R. In alternative embodiments where the seat back portion 24 of the seat assembly 22 is adjustable, one of the adjustment indicators may be assigned to indicate the position of the seat back portion 24. In other types of exercise equipment (for example, equipment having an adjustable chest pad, or the like), an adjustment indicator is assigned to indicate the position of the adjustable portion of the equipment. It should be understood that in exercise equipment having fewer than four adjustable portions, one or more of the adjustment indicators may not be used.

In certain embodiments, the display unit 110 includes a data port recess 160 near the lower right corner of the display unit 110. In certain embodiments, the data port recess 160 is configured to receive a data key 162. In certain embodiments, the data key 162 comprises an integrated circuit 164 and a supporting handle 166. In one embodiment, the integrated circuit 164 on the data key 162 comprises a data device. A compatible interface can be positioned in the data port recess 160 of the display unit 110 to communicate with the integrated circuit 164 when the data key 162 is present. A non-volatile memory within the integrated circuit 164 stores user identification information and advantageously includes historical information related to the user.

In certain embodiments, the control unit enclosure 100 is pneumatically connected to the accumulators 90L, 90R and is thus connected to the charged side of the pneumatic cylinders 82L, 82R. In certain embodiments, the control unit enclosure is also pneumatically connected to a compressed air source (not shown). Within the control unit enclosure 100, a respective inlet valve (shown schematically in FIG. 5, discussed below) for each accumulator 90L, 90R selectively routes compressed air to the accumulator to increase the air pressure in the accumulator and thus increase the air pressure on the charged side of the corresponding pneumatic cylinder. In certain embodiments, each inlet valve comprises two inlet valves of varying sizes. A larger inlet valve is selectively activated by a control system (described below) to increase the volume of air in the cylinder rapidly when the resistance level of a pneumatic cylinder is increased. A smaller inlet valve is selectively activated by the control system to increase the volume of air in the cylinder in finer increments when the control system is maintaining a selected resistance level. Of course, one skilled in the art will appreciate other embodiments can also be used to vary the resistance level.

A respective outlet valve (shown schematically in FIG. 5) for each accumulator is selectively opened to release air to the atmosphere in order to decrease the air pressure on the charged side of the cylinder. In the illustrated embodiment, the outlet valves for both pneumatic cylinders 82L, 82R are controlled by the left actuator button 66L on the left handgrip 60L when a user manually controls the resistance of the two pneumatic cylinders. In certain embodiments, the left actuator button 66L is selectably activated by a user to actuate the outlet valves to reduce the air pressure to the lower chamber of each pneumatic cylinder 82L, 82R.

A user thus can adjust (e.g., increase or decrease) the air pressure within each resistance assembly by operating the appropriate valves using the right actuator button 66R and the left actuator button 66L. In alternative embodiments (not shown), the user can adjust the air pressure using control switches actuated in other ways (e.g., using foot pedals or the like).

Although the right actuator button 66R and the left actuator button 66L could be connected directly to the inlet valves and the outlet valves respectively, in the illustrated embodiment it is preferably that the pressure in the left pneumatic cylinder 82L and the pressure in the right pneumatic cylinder 82R be substantially equal so that the resistance applied to the left handgrip 60L and the resistance applied to the right handgrip 60R are substantially equal. In the illustrated embodiment, this is accomplished by providing a respective actuator signal from each actuator button 66R, 66L to a monitoring or control system 200 (illustrated in block diagrams in FIG. 5 and FIG. 6) that is located within the control unit enclosure 100. Although represented as a single control system, in certain embodiments, the monitoring or control system 200 comprises a plurality of microprocessors programmed to perform specific functions, such as real-time measurement and adjustment of air pressures, real-time measurement of positions and computation of velocities, communicating with the user via the display panel, and the like.

FIG. 5 illustrates a block diagram of an embodiment of a pneumatic system and a monitoring and control system 200 for the exemplary exercise apparatus of FIG. 1 that includes a first configuration of control valves. In the simplified embodiment illustrated in FIG. 5, the monitoring or control system 200 receives the respective actuator signals and determines whether the user is requesting a pressure increase or a pressure decrease. In certain embodiments, the monitoring or control system 200 outputs control signals to a left inlet valve 210L and to a right inlet valve 210R to selectively couple the left accumulator 90L, the right accumulator 90R or both accumulators to a compressed air source 212 to selectively increase the air pressure in one or both accumulators 90L, 90R and the corresponding pneumatic cylinders 82L, 82R. As discussed above, each inlet valve 210L, 210R advantageously comprises a pair of inlet valves. In particular, a large inlet valve in a pair is selectively operated to provide coarse adjustment of the air pressure in the respective pneumatic cylinder. A small inlet valve in a pair is selectively operated to provide fine adjustment of the air pressure in the respective pneumatic cylinder.

In certain embodiments, the monitoring or control system 200 outputs control signals to a left outlet valve 214L and to a right outlet valve 214R to selectively release air from one or both accumulators 90L, 90R to selectively decrease the air pressure in the respective pneumatic cylinders 82L, 82R. In certain embodiments, the inlet valves and the outlet valves are selectively controlled to achieve the desired pressure change while maintaining substantially equal resistances provided by the two pneumatic cylinders 82L, 82R. In certain embodiments, the monitoring or control system 200 accomplishes this by receiving a feedback signal from a left pressure transducer 220L coupled to the left pneumatic cylinder 82L and by receiving a feedback signal from a right pressure transducer 220R coupled to the right pneumatic cylinder 82R. In certain embodiments, the monitoring or control system 200 samples the feedback signals periodically (e.g., at a sample rate of 10 times per second in one embodiment and at a sample rate of 50 times per second in another embodiment having proportional valves) to determine the gage pressures measured in the cylinders. In certain embodiments, the gage pressure is added to the ambient barometric pressure that is also periodically measured using a barometric pressure transducer 224 in order to determine the absolute pressure in each cylinder. In certain embodiments, the absolute pressure in each cylinder is compared to a calculated desired absolute pressure, and the monitoring or control system 200 then adjusts the control signals applied to the inlet valves and outlet valves accordingly to achieve the desired absolute pressure. In alternative embodiments, the barometric pressure transducer 224 is not included, and the barometric pressure is estimated from an altitude setting provided as an input to the monitoring or control system 200.

In certain embodiments, the monitoring or control system 200 outputs control signals to a left outlet valve 214L and to a right outlet valve 214R to selectively release air from one or both accumulators 90L, 90R to selectively decrease the air pressure in the respective pneumatic cylinders 82L, 82R. In certain embodiments, the inlet valves and the outlet valves are selectively controlled to achieve the desired pressure change while maintaining substantially equal resistances provided by the two pneumatic cylinders 82L, 82R. In certain embodiments, the monitoring or control system 200 accomplishes this by receiving a feedback signal from a left pressure transducer 220L coupled to the left pneumatic cylinder 82L and by receiving a feedback signal from a right pressure transducer 220R coupled to the right pneumatic cylinder 82R. In certain embodiments, the monitoring or control system 200 samples the feedback signals periodically (e.g., at a sample rate of 10 times per second in one embodiment and at a sample rate of 50 times per second in another embodiment having proportional valves) to determine the gage pressures measured in the cylinders. In certain embodiments, the gage pressure is added to the ambient barometric pressure that is also periodically measured using a barometric pressure transducer 224 in order to determine the absolute pressure in each cylinder. In certain embodiments, the absolute pressure in each cylinder is compared to a calculated desired absolute pressure, and the monitoring or control system 200 then adjusts the control signals applied to the inlet valves and outlet valves accordingly to achieve the desired absolute pressure. In alternative embodiments, the barometric pressure transducer 224 is not included, and the barometric pressure is estimated from an altitude setting provided as an input to the monitoring or control system 200.

FIG. 6 illustrates a block diagram of another embodiment of a pneumatic system and a monitoring and control system 200 for the exemplary exercise apparatus of FIG. 1 that includes a second configuration of control valves. Many elements of the block diagram in FIG. 6 are similar to corresponding elements of the block diagram in FIG. 5 and are numbered accordingly. In certain embodiments, the following description is directed to the elements of the block diagram of FIG. 6 that are not in FIG. 5.

In FIG. 6, a first left control valve 610L has a first port 612L coupled to the compressed air source 212. In certain embodiments, the first left control valve 610L has a second port 614L coupled to the atmosphere. In certain embodiments, the first left control valve 610L has a third port 616L coupled to a left common galley 620L. In certain embodiments, the first left control valve 610L is controlled by the monitoring or control system 200 to be in one of two modes. In a first mode, the first port 612L is coupled to the third port 616L so that the left common galley 620L is coupled to the compressed air source 212. In the second mode, the second port 614L is coupled to the third port 616L so that the left common galley 620L is coupled to the atmosphere.

In certain embodiments, the left common galley 620L is coupled to a first port 632L of second left control valve 630L and to a first port 642L of a third left control valve 640L. A second port 634L of the second left control valve 630L is coupled to the left accumulator 90L and to the left pressure transducer 220L via a pneumatic tube 636L. A second port 644L of the third left control valve 640L is coupled to the pneumatic tube 636L via an adjustable orifice 646L. Although shown as a separate element, the adjustable orifice 646L may advantageously be included as part of the third control valve 640L.

In certain embodiments, the second left control valve 630L and the third left control valve 640L are controlled by the monitoring or control system 200. In certain embodiments, the second left control valve 630L operates as a high flow valve. In certain embodiments, the monitoring or control system 200 activates the second left control valve 630L to make course adjustments to the volume of air in the accumulator 90L and the pneumatic cylinder 82L. In certain embodiments, the third left control valve 640L operates as a low flow valve. In certain embodiments, the monitoring or control system 200 activates the second left control valve 630L to make fine adjustments to the volume of air in the accumulator 90L and the pneumatic cylinder 82L in accordance with the flow rate determined by the adjustable orifice 640L.

In certain embodiments, the monitoring or control system 200 operates the first left control valve 610L in combination with the second left control valve 630L and the third left control valve 640L. In certain embodiments, the mode of the first left control valve 610L determines whether the volume of air in the left accumulator 90L and the left pneumatic cylinder 82L is being increased or decreased and the selective activation of the second left control valve 630L or the third left control valve 640L determines a rate at which the increase or decrease in volume occurs.

Similarly, a first right control valve 610R has a first port 612R coupled to the compressed air source 212, a second port 614R coupled to the atmosphere, and a third port 616R coupled to a right common galley 620R. In certain embodiments, the first right control valve 610R is controlled by the monitoring or control system 200 to be in one of two modes as described above for the first left control valve 610L.

In certain embodiments, the volume of air in the right accumulator 90R and the right pneumatic cylinder are controlled by a second right control valve 630R having a first port 632R and a second port 634R and third right control valve 642R having a first port 642R, a second port 644R and an adjustable orifice 646R. In certain embodiments, the right accumulator 90R and the right pressure transducer 220R are coupled to the second port 634R of the second right control valve 630R and to the adjustable orifice 646R by a pneumatic tube 636R.

In certain embodiments, the second right control valve 630R and the third right control valve 640R are controlled by the monitoring or control system 200 in combination with the first right control valve 610R to make course adjustments and fine adjustments to the volume of air in the accumulator

90R and the pneumatic cylinder 82R as discussed above for the corresponding left components.

In certain embodiments, the monitoring or control system 200 uses the pressure measurements to calculate the resistive force that will be perceived by a user when the handgrips are moved. In certain embodiments, the calculated resistive force is advantageously displayed as the resistance on the RESISTANCE indicator 120 of the display unit 110 so that a seated user can readily observe the resistance selected by using the left actuator button 66L and the right actuator button 66R. As discussed above, the resistance is displayed as the force (preferably in pounds or kilograms) required to move the handgrips 60L, 60R and is calibrated to be equivalent to the force required to move a corresponding stack of conventional weights.

Once the pressures in the pneumatic cylinders are established by the monitoring or control system 200, the user can apply force to the left handgrip 60L and apply force to the right handgrip 60R to move the handgrips forward. In certain embodiments, the forward movement of the handgrips is coupled via the pivoting action of the left lever 40L and the right lever 40R about the left hinge 32L and the right hinge 32R to cause the left connecting rod 80L and the right connecting rod 80R to move within the left pneumatic cylinder 82L and the right pneumatic cylinder 82R. As discussed in U.S. Pat. No. 4,257,593, incorporated by reference herein, the air within the pneumatic cylinders 82L, 82R and the accumulators 90L, 90R is compressed as the pistons move within the cylinders. In certain embodiments, the force required to compress the air is coupled through the levers to oppose the movement of the handgrips to provide the user with the effect of lifting weights against gravity but without the inertial effects of conventional weights. It will be appreciated that as the pistons move farther into the respective cylinders, the force required to further compress the air increases; however, the shapes of the upper lever portions 44L, 44R are selected such that the user is provided with increasingly more leverage to compensate for the increased air pressure. Thus, the user pushes against substantially the same force throughout each exercise stroke. In certain embodiments, the shapes of the upper lever portions and parameters of other elements can be modified in alternative embodiments to adjust the shape of the force curve in each stroke for specific applications.

In addition to the mechanical control of the force provided by the shapes of the upper lever portions 44L, 44R, the force is also controlled by the monitoring or control system 200, which continues to sample the pressure transducers (e.g., at 10 times or 50 times per second) throughout each exercise stroke and selectively applies control signals to the inlet valves and the outlet valves to maintain the correct pressure in each pneumatic cylinder throughout the exercise stroke. Since the pressure is intended to vary throughout the exercise stroke, the monitoring or control system 200 must also determine the position of each cylinder throughout the stroke. In certain embodiments, this is accomplished by precisely measuring the position of each cylinder. In certain embodiments, the position of the piston within the left pneumatic cylinder 82L is determined by a left position transducer 230L, and the position of the piston within the right pneumatic cylinder 82R is determined by a right position transducer 230R. In certain embodiments, the measurements of the position of the piston within the left pneumatic cylinder 82L and of the piston within the right pneumatic cylinder 82R are used to determine one or more of a PEAK SPEED (e.g., as indicated by indicator 138) and/or an AVERAGE SPEED (e.g., as indicated by indicator 140) of the engagement assembly 40. In certain embodiments, the monitoring or control system 200 monitors the movement of the engagement assembly 40 against the resistance level of the controllable resistance over a plurality of repetitions. In certain embodiments, the monitoring or control system 200 determines the peak speed and/or the average speed for each repetition of the plurality of repetitions. In certain embodiments, the monitoring or control system 200 uses the RESISTANCE (e.g., as indicated by indicator 120), the PEAK SPEED (e.g., as indicated by indicator 138), and/or the AVERAGE SPEED (e.g., as indicated by indicator 140) to determine a relationship between the movement of the engagement assembly 40 by the user over the plurality of repetitions. In certain embodiments, the monitoring or control system 200 uses the relationship to determine the RATE OF FATIGUE (e.g., as indicated by indicator 140) for the tested muscle group. In certain embodiments, the movement of the engagement assembly 40 relates to power. In certain embodiments, the movement of the engagement assembly 40 relates to velocity.

In the illustrated embodiment, each of the position transducers 230L, 230R is implemented by a resistive position transducer having a resolution of 1 part in 16,000,000 and having a linearity of better than 1 percent. In certain embodiments, each position transducer 230L, 230R is sampled 400 times per second to determine the instantaneous position of the piston.

In certain embodiments, the monitoring or control system 200 uses the measured positions of each piston to determine the instantaneous volume of the air in each cylinder. In certain embodiments, the monitoring or control system 200 uses the measured barometric pressure and the measured pressures in each cylinder as inputs and solves the universal gas law equation ten times per second (or fifty times per second in an alternative embodiment having proportional valves) to determine whether to add or remove air from each cylinder to maintain the desired resistance at each position in the exercise stroke. In certain embodiments, the monitoring or control system 200 also measures the supply pressure provided by the compressor (not shown) via a storage accumulator (not shown) to determine the amount of time to open a respective air inlet valve in order to add the proper amount of air to a cylinder.

As further illustrated in phantom in FIGS. 5 and 6, the monitoring or control system 200 for certain embodiments of the exercise apparatus 10 is selectively coupled via the communications cable 102 and the adapter 104 to an external computer system 250. In certain embodiments, the computer system 250 is not utilized in connection with the embodiment described herein and is not discussed in further detail.

In certain embodiments, the apparatus 10 is used for exercising the muscles to increase the performance of the muscles. Although the apparatus 10 can be advantageously used as an exercise device by simply setting the resistance and then moving the handles as if the handles were coupled to conventional iron weights, a unique benefit of the apparatus 10 is not achieved in that manner. Rather, when the apparatus 10 is utilized in accordance with the system and method described below, a user is enabled to determine a rate of fatigue for the tested muscle group.

In accordance with one aspect of the particular embodiment described herein, the data key 162 is an electronic replacement for a hand written exercise card. For each workout, the data key 162 stores the time and date of the workout at each machine, the resistance used during the workout, the number of repetitions during each set, and the version and serial number of the software in the machine being used for a particular workout. In certain embodiments, the data key 162 also stores data related to an endurance or fatigue test if the user selects the endurance or fatigue test mode (described below).

As discussed above, the apparatus 10 can be used as an exercise device only. In particular, the electronic display 110 provides digital indications of the resistance value and the repetition count when a user operates the apparatus 10 without inserting a data key 162 into the data port 160. In certain embodiments, the software in the monitoring or control system 200 calculates the peak speed produced during each repetition and displays that value on the peak speed indicator 138. In certain embodiments, the software also maintains a record of the average speed during the repetitions and displays that value on the average speed indicator 140.

The embodiment described herein provides additional functionality when a user inserts a data key 162 into the data port 160. When the data key 162 is inserted, certain indicators provide additional information to the user that automatically keeps track of the parameters of the exercise routine (e.g., the adjustment settings for a particular machine), thus relieving the user of a burden of maintaining a handwritten exercise card. In addition, the display unit 110 is responsive to the presence of the data key 162 to selectively enable a test mode that is particularly advantageous for assisting a user training to determine their endurance or rate of fatigue.

As discussed above, the repetitions indicator 122 generally displays the current repetition count. However, when the data key 162 is inserted into the data port recess 160, the repetitions indicator 122 displays the current set for a selected time interval following the insertion. In certain embodiments, the set count ranges from 1 to 9 and is signaled by the appearance of 3 horizontal bars in the left digit position instead of a number. In certain embodiments, the number of sets is defined as the number of sets of exercises that have been performed by the same user on the same machine in a four-hour period.

After displaying the set count for a few seconds, the repetitions indicator 122 displays the repetition count for the current set. In certain embodiments, the repetition count advantageously ranges from 0 to 99 in the illustrated embodiment. In certain embodiments, the repetition count may be reset by momentarily depressing both the increase actuator button and the decrease actuator button (e.g., the left actuator button 66L and the right actuator button 66R in the described embodiment or the foot pedals (not shown) in an alternative embodiment).

If the user enables the display 110 and the monitoring or control system 200 to operate in the endurance or fatigue test mode, the test mode indicator 124 displays the character P.

In certain embodiments, the RATE OF FATIGUE indicator 142 can display a rate at which a particular body member or muscle group fatigues. The RATE OF FATIGUE indicator 142 may be active during or after a workout is complete and may show how the user, or a muscle group of the user, has fatigued over the course of the workout. An example embodiment of this indicator is described in FIGS. 7 and 8.

In certain embodiments, the results of endurance or fatigue testing can be displayed on the user display 110. In alternative embodiments, the results are not displayed on the user display 110. Rather, the results are transferred to the external computer system 250 only.

FIG. 7 illustrates a flow chart of an exemplary method for performing an endurance or fatigue test. In certain embodiments, the method employs a relationship between movement of an engagement assembly 40 by the user over a plurality of repetitions to determine a rate of fatigue in accordance. In certain embodiments, the movement of the engagement assembly 40 relates to power. In certain embodiments, the movement of the engagement assembly 40 relates to velocity.

In certain embodiments, the fatigue test can include a resistance, movement of that resistance through a range of motion repeatedly, and a specified end point of the test. For example, the method can begin at block 700 where the fatigue test is initiated. In some embodiments, a user may select a fatigue test, or a begin indicator associated with the fatigue test that is located on the display unit 110 as described in FIG. 4.

At block 702 the user may adjust the controllable resistance to a resistance level that will be used throughout the fatigue test. For example, the resistance could be a set resistance specified for a given test. In certain embodiments, the resistance can be a percentage of body weight or some other variable associated with the user. In some embodiments, the resistance level may be manually entered into the display unit 110. In some embodiments, the resistance level is the level determined for training a muscle group for maximum power generation as described in U.S. Pat. No. 8,052,584 which has hereby been incorporated in its entirety. In some embodiments, steps 700 and/or 702 may be skipped where the level of resistance has been predetermined and associated with the data key 162.

In certain embodiments, the method may then move to block 704 where the movement of the engagement assembly 40 against the resistance level over a plurality of repetitions is monitored. In certain embodiments, the engagement assembly 40 may include the movable components of the apparatus 10 as shown in FIGS. 1-6 (e.g., right lever 40R, left lever 40L) that allow for the performance of a "chest press." In some embodiments, the engagement assembly 40 may include the movable components of any workout equipment, such as, for example, the types available commercially from Keiser Corporation, Fresno, California, including engagement assembly's which allow for a leg press, a leg extension machine, which may include a leg curl machine, a standing hip machine, an abdominal machine, a lower back machine, an upper back machine, a lateral pull down machine, a military press machine, a triceps machine, an arm curl machine, a seated butterfly machine, a seated calf machine, a lateral shoulder raise machine, a squat machine, and a hip abductor machine. Monitoring of such movement may be conducted by transducers (e.g., left position transducer 230L, right position transducer 230R, etc.).

In certain embodiments, the plurality of repetitions of the fatigue test can be measured using various methods. For example, the plurality of repetitions may include a set number of repetitions to be complete. In some embodiments, the plurality of repetitions may be measured over a set period of time as the number of repetitions completed during the set time. In some embodiments, the plurality of repetitions may be measured by a total power generated where the number of repetitions completed in achieving the total power are used. For example, the plurality of repetitions could be measured over a sixty second time period. In another example, the plurality of repetitions could be measured over 50 repetitions. In another example, the plurality of repetitions can be measured by the number of repetitions it takes to generate 8000 W of power. As such, the end point of block 704 can be one or more of time, number of repetitions, total power, or any other metric by which to measure a plurality of repetitions. In certain embodiments, the repetitions can be performed at a maximum velocity of the user. In certain embodiments, a concentric phase of the repetition can be performed at a maximum velocity of the user while the repetitions themselves can be timed. In certain embodiments, the timed repetitions are one per second. In certain other embodiments, the timed repetitions are one per half second or any other duration of time. In certain embodiments, the concentric phase can be timed for a given speed through a Range of Motion (ROM) as well as a time between repetitions.

In certain embodiments, the method may then move to block 706, where, in certain embodiments, data including a peak speed and/or an average speed are determined for each repetition. In certain embodiments, the movement of the engagement assembly 40 may be monitored by transducers, such as transducers 230L, 230R as detailed in FIGS. 5 and 6. Tracking the movement of the engagement assembly 40 over a period of time allows for a velocity of the movement to be determined. In certain embodiments, the data generated by the test can consist of measuring the peak and/or average speed and/or power for each limb for each repetition. In certain embodiments, the data can consist of a total of the peak or average power for each limb for each repetition.

In certain embodiments, the method may then move to block 708, where, in certain embodiments, a relationship between the movement of the engagement assembly 40 by the user over the plurality of repetitions is determined. In certain embodiments, the relationship is determined based on one or more of the RESISTANCE (e.g., as indicated by indicator 120), the PEAK SPEED (e.g., as indicated by indicator 138), and/or the AVERAGE SPEED (e.g., as indicated by indicator 140). In certain embodiments, the movement of the engagement assembly 40 relates to power. In certain embodiments, the movement of the engagement assembly 40 relates to velocity.

In certain embodiments, power may be determined by multiplying the resistance level by the velocity of the engagement assembly 40. In certain embodiments, power levels may be determined using the peak speed and/or the average speed of the engagement assembly 40. In some embodiments, the peak and/or average speed of each repetition may be used to determine the power generated by that repetition. In some embodiments, the peak and/or average speed of several repetitions may be used to determine the power generated per repetition. In some embodiments, the speed of a portion of the repetition may be used to determine the power generated during that portion of the repetition.

In certain embodiments, the method may then move to block 710 where the relationship is used to determine the RATE OF FATIGUE (e.g., as indicated by indicator 142) for the user. In certain embodiments, the rate of fatigue may be presented as the decrease in power and/or velocity per repetition of the test. For example, a graph of the data can be shown to the user which shows the relationship between the power and/or velocity performed per repetition of the plurality of repetitions of the test. In some embodiments, a numerical representation of this data may be presented. In certain embodiments, the graph and/or numerical value can illustrate how the endurance of the user degrades with each repetition. In certain embodiments, the graph shows a percentage of peak and/or average power and/or speed at the end of the test versus the beginning. Further, in some embodiments, a rate of fatigue for a second muscle group may be assessed and compared to the rate of fatigue of the first muscle group. In some embodiments, the first and second muscles groups may be a left and right body member.

An example of an embodiment of a specific implementation of the fatigue test would be a sprint test developed for sprinters and hurdlers. In certain embodiments, the user performs one or more of four different tests on as many as three different machines. In certain embodiments, two of the four tests are 40-second sprints. One test being a power test (heavier resistance) and another test being a dynamic test (lighter resistance). In certain embodiments, the other two tests can be 10-second sprints, one power and the other dynamic. In certain embodiments, the resistance level in the power test and the resistance level in the dynamic test may be based on a percentage of the users bodyweight. In certain embodiments, the goal of each test may be to accomplish as many repetitions as possible in the allotted time. In some embodiments, a clock can start when the first limb of the user begins its second repetition as the first repetition is not counted because it may be slow and could skew the data. In certain embodiments, the test is over upon completion of the last repetition that started before the time (e.g., 10 seconds, 40 seconds, etc.) limit was up.

In certain embodiments, the data that is captured is one or more of Left and Right Peak Velocity or Speed, and/or Power per Rep, Average Power and/or Velocity per Rep, total Left and Right Peak Velocity or speed and/or Power, Average Velocity and/or Power generated during the test. Left may resemble the data collected from the section of the engagement assembly 40 related to the left body member (e.g. body part or specific muscle such as an arm, leg, bicep, calve etc.), and Right may resemble the data collected from the section of the engagement assembly 40 related to the right body member. A mean or average trend line may be graphed of the Power and/or Velocity data collected which may show the change in power and/or velocity generated between each repetition. A comparison may also be presented of the percentage of power generated per repetition at the end of the test compared to the beginning of the test. In some embodiments, the number of repetitions completed within the time limit out of the total repetitions required by the test may be presented.

FIG. 8 illustrates a graphical data output of the endurance or fatigue test performed in accordance with the method of FIG. 7. In certain embodiments, the method uses a relationship between power generated by the user over the plurality of repetitions to determine the rate of fatigue. It should be understood that the relationship between power generated by the user over the plurality of repetitions to determine the rate of fatigue will vary from user to user. In certain embodiments, velocity is used. Thus, the data presented in FIG. 8, such as but not limited to the end points and the slopes of the straight lines, will vary from user to user.

In certain embodiments, the graphing steps described above are performed to generate a visual indication of the foregoing information. In some embodiments, the graphing step is not performed. Rather, the monitoring and control system 200 may determine the data and generate a numerical output which is representative of the foregoing information. In certain embodiments, the graph, and/or numerical data such as described below may be presented to the user through the display unit 110 of FIG. 4. In some embodiments, this data may be recorded and analyzed on the external computer system 250 after the workout has been complete.

In certain embodiments, a user interface 800 may represent the graphical and numerical presentation and analysis of data collected and analyzed for a fatigue test according to an example embodiment. Here, a graph 801 displays a set of recorded repetitions 804 along an x-axis and a set of associated power datapoints 802 along the y-axis. Thus, the power generated per each repetition can be visualized. In some embodiments, the datapoints on the y-axis may be velocity. Further, the graph 801 shows a left plot line 806 and a right plot line 808 of the graphed data points which are associated with the left and right body member or muscle being tested. Further, a left trend line 810 and a right trend line 812 have been graphed over the associated plot lines 806, 808. In certain embodiments, the slope of each of trend line 810, 812 may represent the decrease in power per repetition or the rate of fatigue of each body member or muscle.

According to some embodiments, the user interface 800 may also display a number of repetitions complete 814 within the testing period. For example, in the depicted test results, 68 of the 72 repetitions were completed for the left body member and 68 of 73 repetitions were completed for the right body member. In certain embodiments, the graph may also indicate a percentage of power generated 816 at the end of the fatigue test relative to the power generated at the beginning of the fatigue test. For example, as shown the test ended with left body member generating 32.2% of power and the right body member generating 38.2% of power. In certain embodiments, the user interface 800 may also indicate a total power summary 818 which is indicative of the total power that each body member generated during the course of the test. Here, the total power generate for the left body member was 5533.6 W and the total power generated for the right body member was 6742.8 W. In certain embodiments, the user interface 800 may also include a key 820 which indicates the various aspects of the data presented such as the trend lines, data points, and each body member being tested. In some embodiments, the user interface 800 may include a label 822 which may indicate the name of the user, the exercise being performed (e.g. seated calf raise, chest press etc.), and/or the type of test (e.g. sprint, heavy etc.).

It should be understood that the foregoing description of the apparatus is only one example of a measurement apparatus that can implement the system and method in accordance with aspects of the present invention. For example, one skilled in the art will appreciate that the foregoing features can be advantageously incorporated into a leg conditioning apparatus to determine an endurance or rate of fatigue for the leg. After determining the endurance or rate of fatigue for the muscle group, a suitable conditioning program can be developed to improve the endurance or rate of fatigue to achieve a desired result.

Although described above with respect to athletic ability, it should be understood that the apparatus and method in accordance with aspects of the embodiments of the present invention can be advantageously used in other environments. For example, one problem encountered by a significant portion of an aging population is loss of strength and mobility. Failure to develop and maintain an adequate physical condition while younger becomes a far greater problem as the muscles deteriorate and weaken. It has been shown that strengthening exercises are beneficial to the overall health of an aging individual. However, as discussed above, measurement of strength alone is not sufficient in most cases to properly determine a person's physical ability. The above-described apparatus and method can be advantageously used to determine endurance or rate of fatigue for muscle groups of a user. A conditioning program can then be developed to improve the person's endurance or rate of fatigue rather than simply increasing strength or increasing speed.

The disclosure may be embodied in other specific forms without departing from its spirit or essential characteristics. The described embodiments are to be considered in all respects only as illustrative and not restrictive. The scope of the invention is therefore indicated by the appended claims rather than by the foregoing description. All changes which come within the meaning and range of equivalency of the claims are to be embraced within that scope.

What is claimed is:

1. A method for assessing a rate of fatigue for a muscle group on an exercise apparatus having an engagement assembly movable against a controllable resistance by the muscle group of a user and having a monitoring system that measures a velocity of movement of the engagement assembly, the method comprising:

adjusting the controllable resistance to a resistance level, wherein the controllable resistance is a pneumatic device;

monitoring the velocity of movement of the engagement assembly against the resistance level over a plurality of repetitions, the velocity of movement of the engagement assembly being determined by the user while exercising;

monitoring a pressure within the pneumatic device throughout each repetition of the plurality of repetitions;

selectively changing the pressure within the pneumatic device to maintain the resistance level throughout a Range of Motion (ROM) for each repetition of the plurality of repetitions;

determining a peak speed for each repetition of the plurality of repetitions and/or an average speed for each repetition of the plurality of repetitions;

using the maintained resistance level of the pneumatic device and at least one of the peak speed or the average speed to determine a relationship between the movement of the engagement assembly by the user over the plurality of repetitions; and using the relationship to determine the rate of fatigue.

2. The method of claim 1, wherein the movement of the engagement assembly relates to power.

3. The method of claim 1, wherein the resistance level is selected based on percentage body weight.

4. The method of claim 1, further comprising determining a peak power and/or an average power for each repetition of the plurality of repetitions.

5. The method of claim 4, further comprising displaying the peak power and/or the average power for each repetition of the plurality of repetitions.

6. The method of claim 4, further comprising determining a total of the peak power and/or a total of the average power over the plurality repetitions.

7. The method of claim 6, further comprising displaying the total of the peak power and/or the total of the average power over the plurality repetitions.

8. The method of claim 1, wherein the plurality of repetitions are performed at a maximum velocity.

9. The method of claim 1, wherein a concentric phase of each repetition of the plurality of repetitions is performed at a maximum velocity.

10. The method of claim 9, wherein each repetition of the plurality of repetitions is a fixed time.

11. The method of claim 10, wherein the fixed time is 1 second.

12. The method of claim 10, wherein the concentric phase of each repetition of the plurality of repetitions is timed for a given velocity through the Range of Motion (ROM).

13. The method of claim 1, wherein an end point corresponds to a final repetition of the plurality of repetitions.

14. The method of claim 13, wherein the end point is based on time.

15. The method of claim 13, wherein the end point is based on number of repetitions.

16. The method of claim 13, wherein the end point is based on a total of the peak power and/or a total of the average power.

17. The method of claim 1, further comprising:

assessing a rate of fatigue for a second muscle group; and comparing the rate of fatigue for the muscle group to the rate of fatigue for the second muscle group.

18. A method for assessing a rate of fatigue for a muscle group on an exercise apparatus having an engagement assembly movable against a controllable resistance by the muscle group of a user and having a monitoring system that measures a velocity of movement of the engagement assembly, the method comprising:

adjusting the controllable resistance to a resistance level, wherein the controllable resistance is a pneumatic device;

monitoring the velocity of movement of the engagement assembly against the resistance level over a plurality of repetitions, the velocity of movement of the engagement assembly being determined by the user while exercising;

monitoring a pressure within the pneumatic device throughout each repetition of the plurality of repetitions;

selectively changing the pressure within the pneumatic device to maintain the resistance level throughout a Range of Motion (ROM) for each repetition of the plurality of repetitions;

determining a relationship between the movement of the engagement assembly by the user over the plurality of repetitions; and using the relationship to determine the rate of fatigue.

19. The method of claim 18, wherein the movement of the engagement assembly relates to power.

20. An apparatus for assessing a rate of fatigue for a muscle group, the apparatus comprising:

a controllable resistance set to a resistance level, wherein the controllable resistance is a pneumatic device;

an engagement assembly movable against the controllable resistance by using the muscle group of a user;

a monitoring system configured to:

measure a velocity of movement of the engagement assembly over a plurality of repetitions to determine a relationship between the movement of the engagement assembly by the user over the plurality of repetitions, the velocity of movement of the engagement assembly being determined by the user while exercising, monitor a pressure within the pneumatic device throughout each repetition of the plurality of repetitions, selectively change the pressure within the pneumatic device to maintain the resistance level throughout a Range of Motion (ROM) for each repetition of the plurality of repetitions, and determine the rate of fatigue using the relationship.

21. The apparatus of claim 20, further comprising a display unit that displays the rate of fatigue.

22. The apparatus of claim 20, wherein the engagement assembly comprises a left lever and a right lever.

23. The apparatus of claim 20, wherein the movement of the engagement assembly relates to power.

* * * * *